United States Patent [19]

Oriel et al.

[11] Patent Number: 5,691,171

[45] Date of Patent: Nov. 25, 1997

[54] METHOD FOR PRODUCTION OF INDIGO AND INDIRUBIN DYES

[75] Inventors: Patrick J. Oriel, Midland, Mich.; In Cheol Kim, Taejeon, Rep. of Korea

[73] Assignee: Board of Trustees operating Michigan State University, East Lansing, Mich.

[21] Appl. No.: 546,829

[22] Filed: Oct. 23, 1995

[51] Int. Cl.$^6$ .......................... C09B 7/08; C12N 15/31; C12N 15/52

[52] U.S. Cl. .................. 435/118; 435/190; 435/252.33; 435/320.1; 536/23.2; 536/23.7; 548/653

[58] Field of Search ........................ 435/118, 190, 435/69.1, 320.1, 252.33; 548/653; 536/23.2, 23.7

[56] References Cited

U.S. PATENT DOCUMENTS

| | | | |
|---|---|---|---|
| 4,520,103 | 5/1985 | Ensley | 435/121 |
| 4,894,337 | 1/1990 | Oriel et al. | 435/156 |
| 5,112,747 | 5/1992 | Van Grinsven et al. | 430/321 |

OTHER PUBLICATIONS

Dong et al. Aug. 1992. Applied and Environmental Microbiology 58(8):2531–2535 Aug. 1992.
Gurujeyalakshmi, G., et al., Appl. Environ. Microbiol. 55:500–502 (1989).
Hart et al, Microbiology 138 211–216 (1992).
Kim and Oriel, Applied and Environmental Micro-biology 61 1252–1256 (1995).
Dower, W. J., et al., Nucleic Acids Res. 16:6127–6139 (1988).

Primary Examiner—Keith C. Furman
Attorney, Agent, or Firm—Ian C. McLeod

[57] ABSTRACT

A method for the production of indigo and indirubin dyes using a recombinant *Escherichia coli* containing a gene encoding a phenol hydroxylase from *Bacillus stearothermophilus*. The dyes are used for coloring cloth and the like.

9 Claims, 7 Drawing Sheets

```
                                                              AAGCTTTTGCAAGCG   -541
GTTACATTACGTATCCTGATTTTCCTACCATAACATGGACAGAAGACAAAATCGGTCAAG                   -481
GAATCTTCTATCATAGAAGAGAATTGACGGAGTCATTCATCAAGGCGCTGACATAATCGA                   -421
AAAAGTGAAATATAAGCGAGATAAGAAACATGCCGATTGTTCAAGTACAATTGTTTGG                     -361
AAGTCTTACCGTTGAGCAGAAGAGGCATTAATAAACGTCGGATGCAGTAGCCCG                         -301
TGTCTTACATGCTCCATTAATCCGTGTGCTGATTCAAGAGATGCCGGGAAAA                           -241
CTGGGCATTGCCGGAGAATCCGCACAAAGAAACTGGGCAGGCGCCAGGAAATAGT                        -181
TATATCCAGCGCAAGCGCTGAAAAAGATTTGTTTGTTGTAAGCGCTGTCAATATGCT                      -121

GCGGTACATCTTCCATAAGGAAGGAGGCAGGCCGGTTCAGGCGGTTTGCCTTCTCTTAAAT                   -61
ATATATCTATCTAAGGAGAACATAGTTTTCTAATAACATGTTAAAGGAGGAAACACAA                      -1
+1
ATGGAAAAAAATAAAATGTTAATAGAAGAAAAGTTGGACACTGCTGCTCTTCTTGCTAAG                    60
 M  E  K  N  K  M  L  I  E  E  K  L  D  T  A  A  L  L  A  K          20
GCGGAGGAAATAGGCCGGATTGCTGAGGAAGAGGCGGTGAAGCGGACCGCAATGCCTGT                    120
 A  E  E  I  G  R  I  A  E  E  E  A  G  E  A  D  R  N  A  C          40
TTCTCCGACCGGGTGGCTAGGGCCATTAAAGAAGCTGGAATTCCACACAAGCTCATGCGTCCC                180
 F  S  D  R  V  A  R  A  I  K  E  A  G  F  H  K  L  M  R  P          60
AAGCAGTACGGAGGACTGCAAGTAGACCTGCGAACTTACGGGGAGATTGTCCGCACAGTG                   240
 K  Q  Y  G  G  L  Q  V  D  L  R  T  Y  G  E  I  V  R  T  V          80
GCCCGGTACAGTGTTGCCGCAGGATGGCTGACCTATTTTTATTCCATGCATGAGGTTTGG                   300
 A  R  Y  S  V  A  A  G  W  L  T  Y  F  Y  S  M  H  E  V  W         100
GCTGCATATCTGCCTCCAAAGGCAGAGAGAAATTTTGGACAAGGAGGGCTGTTGGCA                      360
 A  A  Y  L  P  P  K  G  R  E  E  I  F  G  Q  G  G  L  L  A         120
GACGTCGTTGCCCCTGTTGGCCGGGTGGAGAAGGACGGGCTACCGTCTCTATGG                         420
 D  V  V  A  P  V  G  R  V  E  K  D  G  D  G  Y  R  L  Y  G         140
CAGTGGAACTTCTGTAGCGGTGTCCTCCATAGTGACTGTTGTAGTGCCTAAGTCGGATGATG                 480
 Q  W  N  F  C  S  G  V  L  H  S  D  W  I  G  L  G  A  M  M         160
GAGCTGCCTGACGGCAATAGTCCTGAGTACTGTTTGTTAGTGCCTAAGTCGGATGTC                      540
 E  L  P  D  G  N  S  P  E  Y  C  L  L  V  P  K  S  D  V           180
CAGATCGTAGAAAATTGGGATACCATGGGCCTTCGGGAAGCAACGGGGTATTA                          600
```

FIG. 6A

```
Q  I  V  E  N  W  D  T  M  G  L  R  A  S  G  S  N  G  V  L                    200
GTTGAAGGTGCTTATGTTCCATTACACCGGATCTTTCCGGCTGCCGGGTGATGGCTCAT                   660
V  E  G  A  Y  V  P  L  H  R  I  F  P  A  G  R  V  M  A  H                    220
GGGAAGCCAGTGGGAGGCGATTACGACGAGAATGATCCGTATATCGCATGCCATTATG                    720
G  K  P  V  G  G  D  Y  D  E  N  D  P  V  Y  R  M  P  F  M                    240
CCGCTTTCTTGTTCTTGGTTCCCTTAGTATCTTTAGGCGGCGAACGATTGGTGTCA                      780
P  L  F  L  L  G  F  P  L  V  S  L  G  G  D  E  R  L  V  S                    260
CTTTTCCAAGAACGCACTGAGAAGCGCATTCGTCTTCAAGGCGGCGCAAAGGAAAAG                     840
L  F  Q  E  R  T  E  K  R  I  R  V  F  K  G  G  A  K  E  K                    280
GATTCTGCCGCTAGCCAGCGCTGTGTTAGCCGAGATGAAAACAGAATTAAATGCAATGAA                  900
D  S  A  A  S  Q  R  L  L  A  E  M  K  T  E  L  N  A  M  E                    300
GGCATTGTGGAACAATATATCCGCCAGCTTGAGGCTTGCCAAAAGGAAGAAGACGGTG                    960
G  I  V  E  Q  Y  I  R  Q  L  E  A  C  Q  K  E  G  K  T  V                    320
ATGAACGATATGGAGCGAGAGCAGCTATTCGCATGGCGTGGATATGTGGCAAAGCGTCC                  1020
M  N  D  M  E  R  E  Q  L  F  A  W  R  G  Y  V  A  K  A  S                    340
GCCAATATTGCCGTCAGAACACTGTTAACTCTTGGAGGCAATTCGATCTTTAAAGGCGAT                 1080
A  N  I  A  V  R  T  L  L  T  L  G  G  N  S  I  F  K  G  D                    360
CCGGTAGAACTGTTCACAAGAGATTTGCTAGCGGTGGCCGCACATCCTAACTCCCTGTGG                 1140
P  V  E  L  F  T  R  D  L  L  A  V  A  A  H  P  N  S  L  W                    380
GAGGATGCGATGGCTGCATATGGAAGAACGATATTCGGGCTGCCAGGGACCCAGTCTGG                  1200
E  D  A  M  A  A  Y  G  R  T  I  F  G  L  P  G  D  P  V  W                    400
TAAGACAGCAGCAGAATGTGTGTTATAAGATTTCAAAAAATTCATTTCTTTGGTGAA                    1260
* * *
AGAAAATGGATTTCACACAAATTAAACCAATGAACCCAATTGGATCGTTCGCGTCCAT                   1320
TTCACCAATAATATACAAAAAAACAGCAGAAAAGGAGACGGATACCGGTGATGACCGTTTGT              1380
TTCGCAACGTAATGGGACATTTGCCACAGGGTGACAGTCATAACGACAGAGATCGACG                   1440
GGGATATACACGGCATGACTGCAAATGCGTTTATGTCCGTTATCATCCAAAATTGG                     1500
TGCTTATTTCGATTGGCGAAAAAGCAGTATCAAAAAATGAAAACGT                               1560
ATGCAGTAAGCTT                                                                1573
```

METHOD FOR PRODUCTION OF INDIGO AND INDIRUBIN DYES

BACKGROUND OF THE INVENTION (1) Field of the Invention

The present invention relates to a method for the production of indigo and indirubin dyes using a novel recombinant *Escherichia coli* containing a gene encoding a phenol hydroxylase from *Bacillus stearothermophilus*. The dyes are used for coloring cloth and the like as is well known to those skilled in the art.

(2) Description of Related Art

Aerobic thermophilic bacteria are a subject of research attention as a result of interest in their evolution, survival mechanisms, and potential for biotechnological utilization. *Bacillus stearothermophilus* is a well known bacterium of this type. Degradation of phenol by a *Bacillus stearothermophilus* has been described in the prior art (Gurujeyalakshmi, G., et al., Appl. Environ. Microbiol. 55:500–502 (1989)).

U.S. Pat. No. 4,894,337 to Oriel et al., one of the inventors herein, describes *Bacillus stearothermophilus* BR219 which is deposited under the Budapest Treaty as ATCC 67824. This strain produces a phenol hydroxylase which converts a benzene ring compound (phenol) to a cyclic hydroxide (pyrocatechol).

U.S. Pat. No. 4,520,103 to Ensley describes a method for production of indigo with a recombinant bacterium in a medium which is indole free. Use of specific strains of a recombinant *E. coli* to produce indigo or indigotin from indole is particularly described using a gene encoding an aromatic dioxygenase from another bacterium to convert the indole. Indirubin production is not described. Indole preparation is described in U.S. Pat. No. 5,112,747 to Van Grinsyen et al. Hart et al (Microbiology 138 211–216 (1992) described a recombinant *E. coli* containing a cloned Rhodococcus gene for producing indigo and indirubin. Indole is produced which is oxidized to indigo.

The formula for indole is:

The formula for indigo is:

As can be seen the conversion to indigo requires a condensation of two moles of indole. The same type of condensation is required for forming indirubin which is an isomer having the formula:

It is likely that all conversions first require the formation of indole or a closely related compound.

OBJECTS

It is therefore an object of the present invention to provide a novel method for the preparation of indigo and indirubin. Further, it is an object of the present invention to provide novel bacteria, plasmids and DNA involved in the conversion. Further still, it is an object of the present invention to provide a method for producing indigo and indirubin which is relatively easy to perform and inexpensive. These and other objects will become increasingly apparent by reference to the following description and the drawings.

BRIEF DESCRIPTION OF THE DRAWINGS

FIGS. 6A and 6B show the nucleotide and deduced amino acid sequence of the phenol hydroxylase gene (SEQ ID NO. 1; pheA). The nucleotide sequence was numbered from the first nucleotide for translation initiation. A putative promoter (−35 and −10 region) and probable Shine-Dalgarno sequence are indicated by boldface type. The inverted repeat sequence upstream and downstream of the coding region are marked with a dashed line.

DESCRIPTION OF PREFERRED EMBODIMENTS

A process for preparation of indigo and indirubin dyes which comprises: growing a recombinant *Escherichia coli* containing a gene from *Bacillus stearothermophilus* encoding phenol hydroxylase in an aqueous growth medium so that indigo and indirubin are produced from the indole.

The cells are grown in an aqueous growth medium preferably containing the phenolic compound, preferably phenol, cresols or chlorophenol as an inducer for phenol hydroxylase. Preferably the phenolic compound is present in an amount between about 0.001 and 10 mM. The yield of the phenol hydroxylase is increased in this manner. Also included is a carbon source, a nitrogen source and minerals. A preferred growth medium is LB which contains yeast extract, sodium chloride and tryptone.

Various organic solvents can be used to extract the indigo and indirubin dyes expressed by or in the cells of the recombinant *E. coli*, such as chloroform and ethyl acetate and other solvents for the indigo and indirubin. The cells can optionally be disrupted by various techniques such as sonication or freezing. The indirubin and indigo can be separated chromatographically by various well known methods.

The present invention also relates to an isolated and purified DNA encoding a phenol hydroxylase having a DNA sequence essentially as set forth in SEQ ID NO:1.

The present invention also relates to a recombinant plasmid containing a segment of DNA encoding a phenol hydroxylase having a sequence essentially as set forth in SEQ ID NO:1.

The present invention also relates to an *Escherichia coli* containing a recombinant plasmid containing a segment of DNA having a sequence essentially as set forth in SEQ ID NO:1.

The present invention also relates to a recombinant plasmid containing a segment of DNA encoding an isolated and purified phenol hydroxylase wherein the DNA is contained in plasmid pGG01 of *Bacillus stearothermophilus* deposited as ATCC 67824.

The present invention also relates to an *Escherichia coli* containing a recombinant plasmid containing a segment of DNA encoding an isolated and purified phenol hydroxylase, wherein the DNA used to produce the recombinant is contained in plasmid pGG01 of *Bacillus stearothermophilus* deposited as ATCC 67824.

Figure 1:
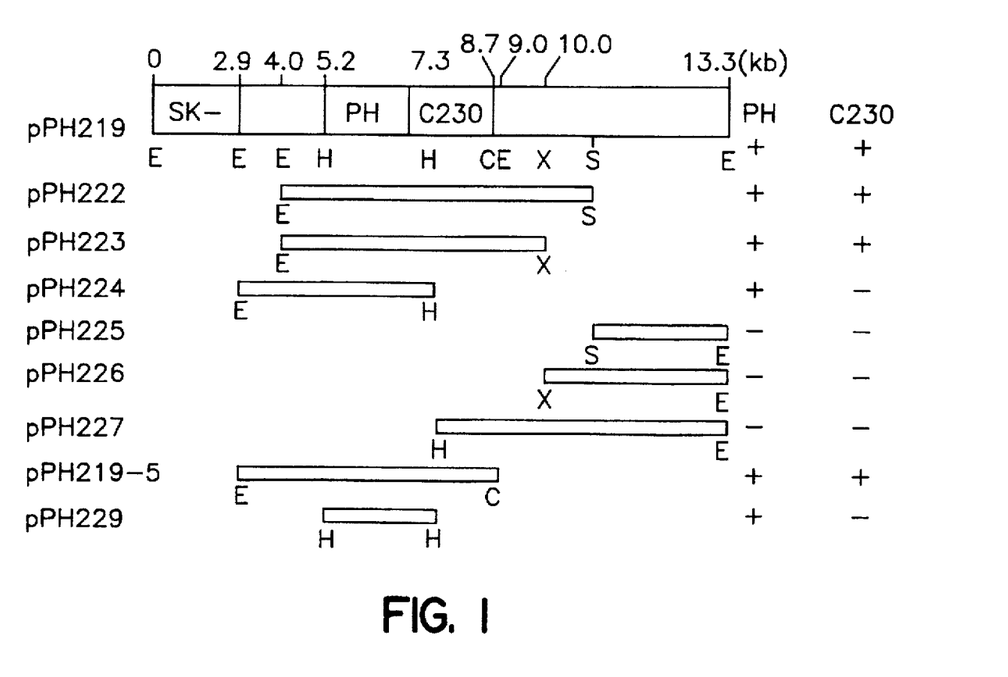
FIG. 1 is a restriction enzyme map of plasmid pPH219 and its derivatives. The ability (+) or inability (−) of the plasmids to produce phenol hydroxylase (PH) and/or catechol 2,3-dioxygenase (C230) is indicated to the right of the restriction enzyme maps. Abbreviations: E, EcoRI; C, ClaI; H, HindIII; X, XhoI; S, SalI. Approximate positions of the phenol hydroxylase and catechol 2,3-dioxygenase genes deduced from this data are shown in the top line of boxes.

The present invention also relates to *Escherichia coli* containing plasmid pPH229 was deposited under the Budapest Treaty as ATCC 69891 at the American Type Culture Collection, Rockville, Md. It is available upon request by name and deposit number. Plasmid pPH229 which encodes for phenol hydroxylase pH as shown in FIG. 1. *Bacillus stearothermophilus* ATCC 67824 is also deposited under the Budapest Treaty. This strain is described in U.S. Pat. No. 4,894,337 to Oriel et al. A publication by the inventors herein described the phenol hydroxylase gene (Kim and Oriel, Applied and Environmental Microbiology 61 1252-1256 (1995)).

The phenol hydroxylase (PH) is isolated from cells of the *Bacillus stearothermophilus*. It can be purified by conventional techniques such as affinity chromatography and gel electrophoresis.

The PH is preferably produced by *E. coli* as a host microorganism using the DNA set forth in SEQ ID NO:1 (FIGS. 6A and 6B). *E. coli* which is commonly used for this purpose as is well known to those skilled in the art. The phenol hydroxylase has the deduced amino acid sequence as set forth in SEQ ID NO:1 (FIGS. 6A and 6B).

The DNA of SEQ ID NO:1 is incorporated into a plasmid (vector) and then transformed into the host microorganism. This can be done by electroporation, transfection and other well known methods of DNA transfer. The DNA used to produce the recombinant is contained in pGG01 of *Bacillus stearothermophilus* deposited as ATCC 67824. The phenol hydroxylase is contained in a 2.1 kb HindIII segment (pPH229; in ATCC 69891) or EcoR1 133 kb segment (pPH219) of pGG01. The host microorganism is *E. coli* as previously discussed.

EXAMPLE 1

The catabolic gene pheA coding for the conversion of phenol to catechol was cloned from *Bacillus stearothermophilus* BR219 into *Escherichia coli*. Following its localization on the 11-kb *B. stearothermophilus* DNA insert by deletion and expression analysis, the phenol hydroxylase gene pheA was subcloned as a 2-kb HindIII fragment, whose transformant expressed the enzyme after phenol induction and even more strongly after o-, m-, and p-cresol induction. In vitro transcription-translation experiments indicated that the phenol hydroxylase and catechol 2,3-dioxygenase enzymes are constituted of single subunits with molecular weights of 44,000 and 33,000, respectively. Nucleotide sequencing of the pheA gene revealed a significant similarity to flavin hydroxylases from Rhodococcus and Streptomyces species. Hybridization experiments indicated that the fragment containing PheA and PheB is located on a 66-kb plasmid, pGG01, in the parental thermophile.

Materials and Methods

Bacterial Strains and Culture Conditions.

*Bacillus stearothermophilus* BR219, an isolate obtained from contaminated river sediment, was maintained at 55° C. in DP minimal medium which is:

| | |
|---|---|
| $K_2HPO_4$ | 0.5 g/l |
| $NH_4Cl$ | 1.0 g/l |
| $MgSO_4.7H_2O$ | 20 mg/l |
| Yeast Extract | 0.2 g/l |
| Casamino Acids | 0.1 g/l |
| pH 7.2 | | containing 5 mM phenol as the major carbon source as previously described (Gurujeyalakshmi, G., et al., Appl. Environ. Microbiol. 55:500–502 (1989)). *Escherichia coli* XL-1 (recA (recAI lac endAI gyrA96 thi hsdR17 supE44 relA1 (F′ proAB, lacIg, lacZIΔM15, Tn10))) (Bullock, W. O., et al., BioTechniques 4:376–379 (1987)), used for construction and maintenance of plasmids, was cultured at 37° C. on LB medium which is:

10 g/l Bacto-tryptone[1]

5 g/l Bacto-yeast extract[2]

10 g/l NaCl pH 7.4

Plasmids were introduced into *E. coli* XL-1 by electroporation (Dower, W. J., et al., Nucleic Acids Res. 16:6127–6139 (1988)). Ampicillin at 50 µg/ml was used for selection of plasmids. Tetracycline at 12.5 µg/ml was also incorporated during growth of the *E. coli* XL-1 host as a precaution against contamination.

[1]Tryptophan source, Difco, Detroit, Mich.
[2]Nitrogen source, Difco, Detroit, Mich.

Genetic Procedures.

Plasmid DNA was isolated from *E. coli* by alkali lysis (Birnboim, H. C., et al., Nucleic Acids Res. 7:1513–1523 (1979)). *B. stearothermophilus* BR219 DNA was prepared by the method of Saito and Miura (Saito, H., et al., Biochim.

Biophys. Acta 72:619–629 (1963)). DNA fragments were isolated from agarose gels by using USBioclean (United States Biochemical Corp. Cleveland, Ohio) and electroelution (IBI, New Haven, Conn.). Restriction enzymes, DNA ligase, and alkaline phosphatase were obtained from Boehringer Mannheim Co., Indianapolis, Ind. Southern hybridizations were performed as described by Maniatis et al (Maniatis, T., et al., Molecular cloning: a laboratory manual. Cold Spring Harbor Laboratory, Cold Spring Harbor, N.Y. (1982)) with American H-bond nylon membrane probed with DNA labelled with ($\alpha$-$^{32}$P)dCTP, using a Boeringer-Mannheim Co. random-primer labeling kit. Following hybridization, blots were washed at high stringency (43° C. in 0.1×SSC-0.1% sodium dodecyl sulfate (SDS)-50% formamide, where 1×SSC is 0.15M NaCl with 0.015M sodium citrate).

Screening for Transformants Carrying PheA and PheB.

Transformants were spread on LB plates containing 1 mM phenol, 50 µg of ampicillin per ml, and 12.5 µg of tetracycline per ml and incubated overnight at 37° C. Colonies that became yellow (as a result of 2-hydroxymuconic semialdehyde) following spraying of a 0.1% of catechol solution were patched on LB plates containing 1 mM phenol. Colonies in which the yellow compound formed during growth without catechol addition were retained as putative carriers of both pheA and pheB.

Preparation of Cell Extracts and Enzyme Assays.

Cells for enzyme analysis were grown in LB broth with 1 mM phenol and 50 µg of ampicillin per ml at 37° C. to mid-log phase, reinoculated into fresh medium of the same composition, and grown to late-exponential phase. The cells were harvested by centrifugation at 6,000×g for 10 min, washed twice in 50 mM sodium phosphate buffer (pH 7.5), disrupted sonically by six 30-s bursts with an ultrasonic homogenizer (Cole-Palmer Instrument co., Chicago, Ill.), and centrifuged at 12,000×g for 30 minutes. The clear supernatant was used as a crude enzyme extract. Phenol hydroxylase was assayed in the supernatant as described by Gurujeyalakshmi and Oriel (Appl. Environ. Microbiol. 55:500–502 (1989)). Catechol 2,3-dioxygenase was assayed as described by Nozaki (Nozaki, M., Methods Enzymol. 17A:522–525 (1970)). Protein was measured by the method of Lowry et al (Lowry, O. H., et al., J. Biol. Chem. 193:265–275 (1951)) with bovine serum albumin for standardization. One unit of enzyme activity is defined as the amount causing the disappearance of 1 µmol of phenol per min at 55° C. for phenol hydroxylase or the appearance of 1 µmol of 2-hydroxymuconic semialdehyde per min at ambient temperature for catechol 2,3-dioxygenase.

Nucleotide Sequence Determinations.

Plasmid vector pBluescript SK- (Stratagene, LaJolla, Calif.) was used to construct the subclones for DNA sequencing. Serial deletion of subclones was made by using the exo/mung system (Stratagene). Nucleotide sequences were determined directly from plasmids by the dideoxy-chain termination method (Sanger, F., et al., Proc. Natl. Acad. Sci. USA 74:5463–5467 (1977)) with T7 DNA polymerase (Sequenase; United States Biochemical Corp.). The dITP was substituted for dGTP to eliminate band compression in GC-rich regions. Wedge gels 0.2 to 0.6 mm thick were used in electrophoresis to increase resolution. Other sequencing procedures were performed by published methods (Maniatis, T., et al., Molecular cloning: a laboratory manual. Cold Spring Harbor Laboratory, Cold Spring Harbor, N.Y. (1982)). Nucleotide and deduced amino acid sequences were analyzed by the GCG DNA analysis program (Genetics Computer Group, Inc., Madison, Wis.).

In Vitro Transcription-Translation and Activity Staining of the SDS-Polyacrylamide Gel.

The protein products of cloned B. stearothermophilus DNA inserts were identified with a DNA-directed transcription-translation system involving E. coli cell extracts (Amersham Life Sciences, Arlington Heights, Ill.). Proteins produced from plasmids (1 µg per reaction) were radioactively labeled with L-($^{35}$S) methionine in 50-min incubation periods and a 30-min (cold) methionine chase reaction. Samples were separated on SDS-10% polyacrylamide gels and protein bands were observed by radioautography. The catechol 2,3-dioxygenase band was located by formation of yellow 2-hydroxymuconic semialdehyde formed after gel immersion in 0.1% catechol. Prestained protein molecular size markers (GIBCO BRL, Life Technologies, Inc. Gaithersburg, Md.) were used.

Nucleotide Sequence Accession Number.

The GenBank accession number of pheA is U17960.

Results

Cloning and expression of pheA.

Mixed plasmid and chromosomal DNA was extracted from B. stearothermophilus BR219 and partially cleaved with EcoRI, and fragments ranging from 9 to 20 kb were obtained by gel electrophoresis and electroelution for ligation with pBluescriptI SK-. Transformants of E. coli XL-1 were grown on LB plates containing ampicillin and phenol and those demonstrating 2-hydroxymuconic semialdehyde formation after being sprayed with 0.1% catechol were retained as putative transformants carrying the pheB gone. Subsequent examination of these transformants yielded EC390, a recombinant which did not grow on phenol but demonstrated production of 2-hydroxymuconic semialdehyde on LB plates containing 1 mM phenol, suggesting the presence of both pheA and pheB encoding the first two steps of the phenol pathway. The plasmid isolated from this recombinant, designated pPH219, contained a 13.3 kb EcoRI insert. To locate pheA and pheB within this insert, measurements of phenol hydroxylase and catechol 2,3-dioxygenase in transformants with insert deletions were carried out by using determined restriction sites. As shown in FIG. 1, both pheA and pheB were located in the 6-kb EcoRI-ClaI DNA fragment cloned in plasmid pPH219-5, and pheA was found in the 2.1 kb HindIII DNA fragment cloned in plasmid pPH229.

Localization of pheA and pheB in B. stearothermophilus BR219.

Figure 2:
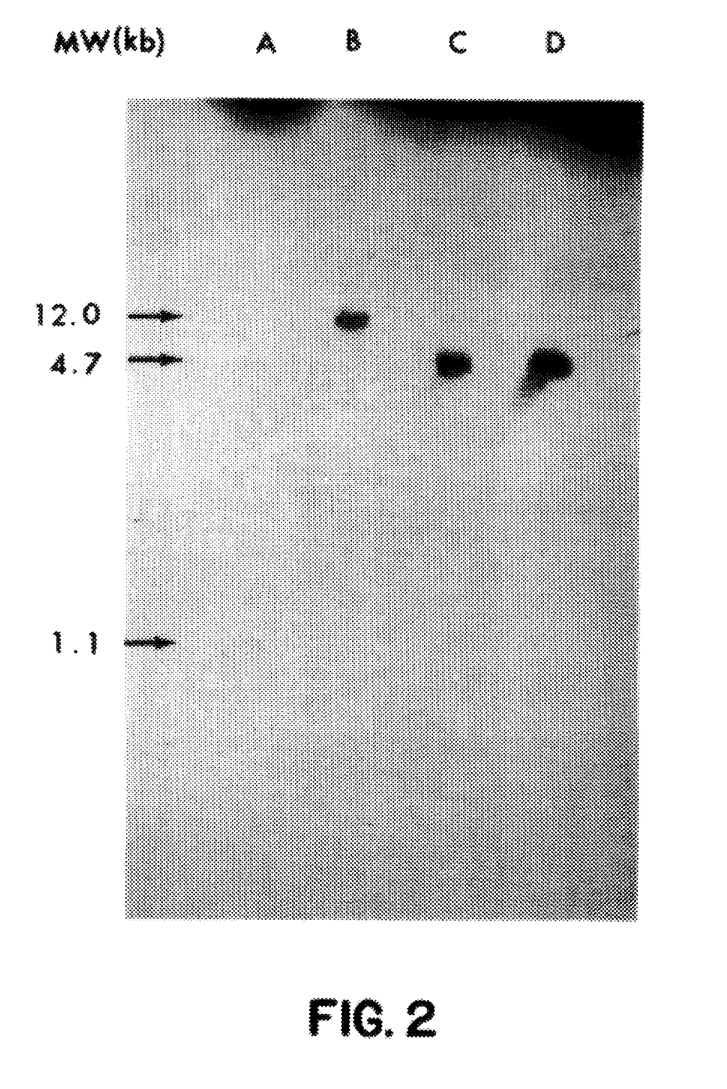
FIG. 2 is a Southern blot analysis of genomic DNA and the cryptic plasmid pGG01 which hybridized with the cloned DNA containing pheA and pheB which was labeled with [α-$^{32}$P] dCTP. Lanes A, EcoRI-digested BR219 genomic DNA; B and C, BamHI- and EcoRI-digested cryptic plasmid pGG01; D, EcoRI-digested pPH219.

B. stearothermophilus BR219 carries a 66-kb low-copy-number plasmid designated pGG01. With the 10.3-kb EcoRI insert of plasmid pPH219 as a probe, Southern hybridization analysis was carried out with EcoRI and BamHI-digested BR219 genomic and plasmid DNA. The cloned insert carrying pheA and pheB hybridized with plasmid but not chromosomal DNA (FIG. 2), indicating that plasmid pGG01 encodes at least part of the phenol catabolic pathway.

Structural Analysis of the Phenol Hydroxylase Gene and Gene Product.

Figure 3:
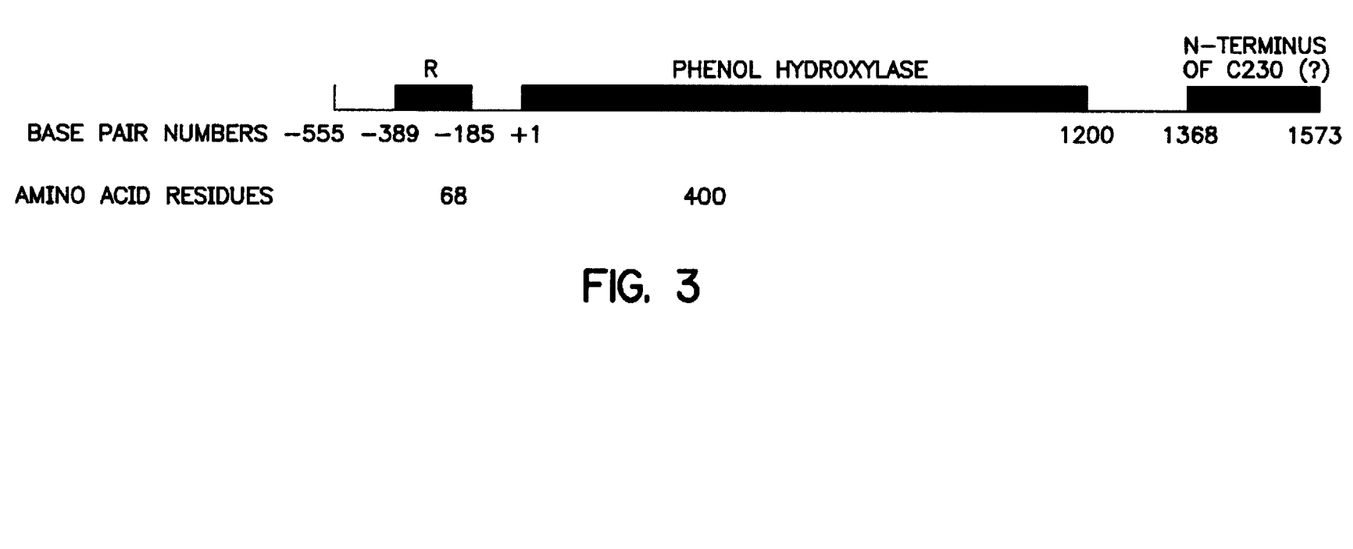
FIG. 3 is a map showing a structural analysis of the 2.1-kb HindIII fragment. R designates an ORF of unknown function. C230 is catechol 2,3-dioxygenase.

To determine the structure of the phenol hydroxylass gens, nucleotide sequencing of the 2.1-kb HindIII fragment (pPH229) was carried out. As shown in FIGS. 6A and 6B (SEQ ID NO:1), one open reading frame (ORF) was found encompassing 1,200 nucleotides encoding a protein of 400 amino acids. The insert also contains about 556 and 373 bp of 5'- and 3'-flanking sequences, respectively. Putative promoter regions, TATATATCTAT and TAATAA, are present from −61 to −51 and from −29 to −24, respectively, from the translational initiation site. A putative Shine-Dalgarno sequence, GGAGAA, was present at the −13 position. The sequence revealed two small additional open reading frames (FIG. 3). The first ORF is upstream of pheA, starting at −389 and ending at −185, with putative promoter regions from −472 to −466 (TATCATA) and from −428 to −423 (ATAAT) and Shine-Dalgarno sequence (−414 to −409 (GCGAGG)). The function of this short ORF, which is designated R, is not known. Another ORF starts downstream of pheA at 1368 without termination. Since the deletion experiments indicated that pheB was in proximity downstream of pheA, it is possible that this is the N terminus of the catechol 2,3-dioxygenase gene.

TABLE 1

Induction of phenol hydroxylase and catechol 2,3-dioxygenase in *E. coli*

| Plasmid | Act of phenol hydroxylase (U/mg of protein) | | Act of catechol 2,3-dioxygenase (U/mg of protein) | |
|---|---|---|---|---|
|  | −phenol | +phenol | −phenol | +phenol |
| SK-1 | 0 | 0 | 0 | 0 |
| pPH219-5 | 0.42 | 0.54 | 0.57 | 0.74 |
| pPH222 | 0.88 | 1.07 | 0.59 | 0.84 |
| pPH223 | 1.11 | 0.83 | 0.67 | 0.97 |
| pPH224 | 0.87 | 0.9 | 0 | 0 |
| pPH229 | 0.12 | 0.72 | 0 | 0 |

Molecular Mass of Phenol Hydroxylase and Catechol 2,3-Dioxygenase.

Figure 4:
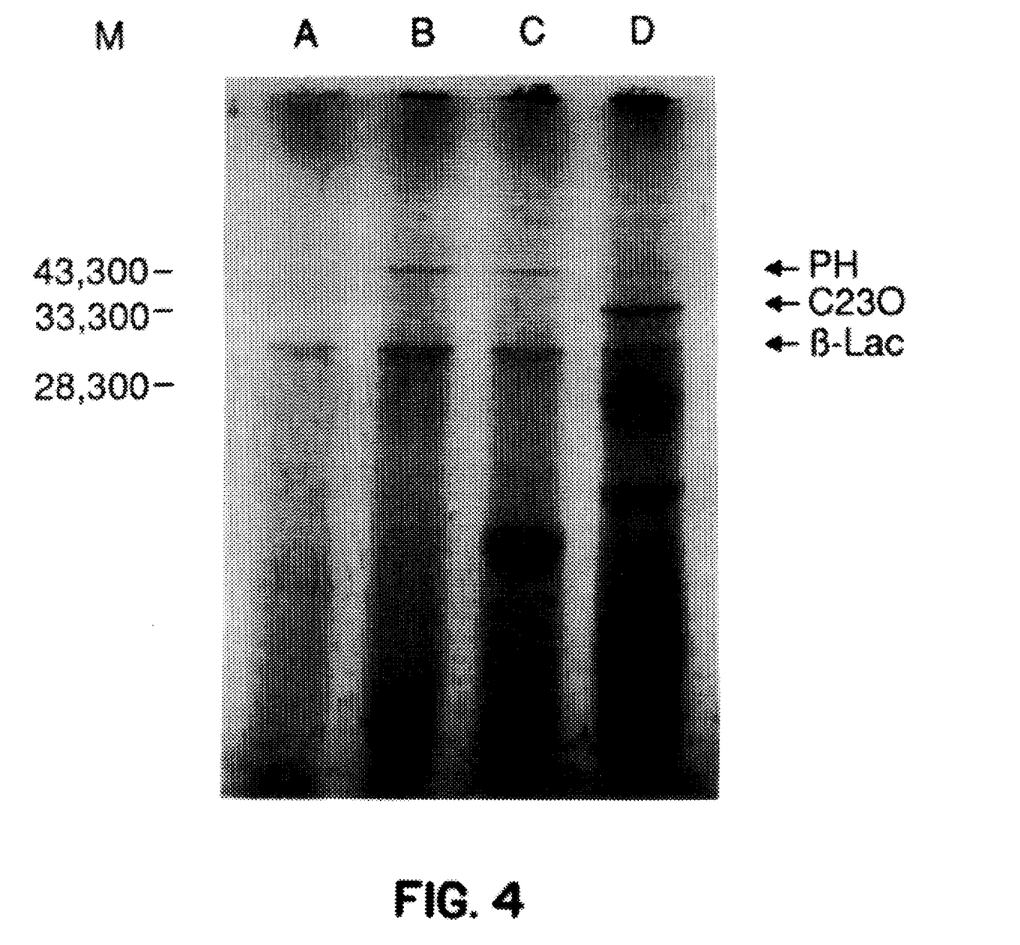
FIG. 4 is an electrophoresis gel showing proteins synthesized by in vitro transcription-translation. Lanes: M, molecular weight markers; A, pBluescript SK- vector; B, pPH229; C, pPH224; D, pPH223. The upper, middle, and lower arrows point to the phenol hydroxylase (PH), catechol 2,3-dioxygenase (C230), and β-lactamase (β-Lac), respectively.

Transcription-translation results (FIG. 4) indicated a protein of 43,000 Da expressed from pPH229, which encodes the pheA gene. This value is in excellent agreement with the 43,000 Da deduced from pheA sequencing data. For pPH223, which encodes both pheA and pheB, an additional 33,000-Da band is seen. Activity staining by gel immersion in 0.1% catechol, yielding yellow 2-hydroxymuconic semialdehyde, was used for identification of this protein as the pheB transcription-translation product (data not shown). The lower-molecular-mass band in FIG. 4, lane C, may also be the product of pheB, which is truncated in pPH224. Other lower-moelcular-mass bands expressed in lanes C and D by subclones containing DNA regions upstream and downstream, respectively, of the sequenced insert of pPH229 have not been identified.

Expression and Inducibility of Phenol Hydroxylass and Catechol 2,3-Dioxygenase Genes in *E. Coli*.

Figure 5:
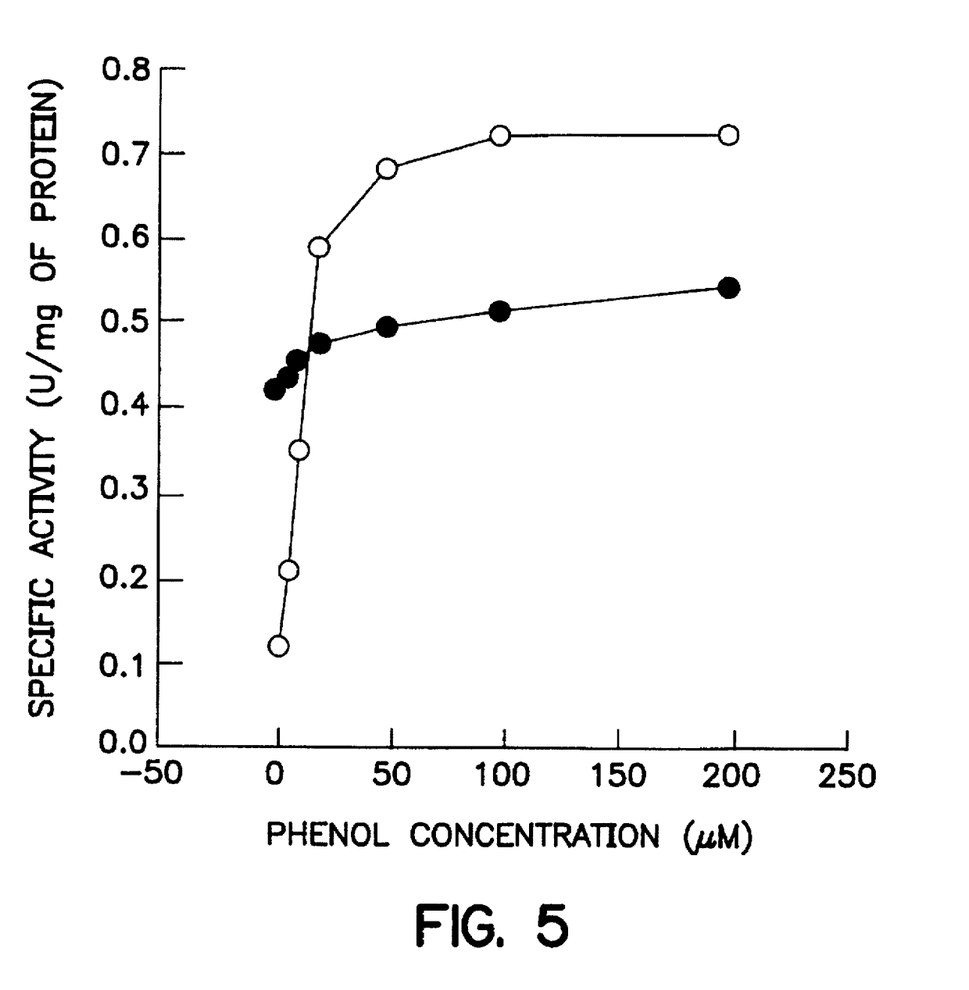
FIG. 5 is a graph showing the effect of phenol concentration on phenol hydroxylase induction. O, phenol hydroxylase produced by *E. coli* containing pPH229; ●, phenol hydroxylase produced by *E. coli* containing pPH219-5.

The phenol path in the BR219 thermophile parent is induced by phenol (Gurujeyalakshmi, G., et al., Appl. Environ. Microbiol. 55:500–502 (1989)). To determine whether the cloned insert in pPH219 contained phenol regulatory elements from parental BR219, transformants containing this plasmid and those of the deletions shown in FIG. 1 were tested for differences in phenol hydroxylase expression in cells grown at different phenol concentrations. As shown in Table 1, in *E. coli* bearing plasmid pPH219 or most of the deletions, phenol hydroxylase and catechol 2,3-dioxygenase specific activities were either unaltered or only slightly increased by growth in the presence of phenol. In pPH229, however, phenol hydroxylase expression demonstrated marked dependence on phenol. A comparison of differences in phenol hydroxylase induction for pPH229 and pPH219-5 with phenol concentration is presented in FIG. 5, which shows that pPH229 demonstrates marked phenol dependence at concentrations up to 20 µM. The level of induction of phenol hydroxylase in this pPH229 by other aromatics is shown in Table 2, which shows that enzyme levels induced by o-, m-, and p-cresol were even higher than that induced by phenol.

TABLE 2

Induction of phenol hydroxylase by aromatic compounds

| Inducer | sp act of phenol hydroxylase (U/mg of protein) |
|---|---|
| None | 0.12 |
| Phenol | 0.54 |
| Benzoate | 0.11 |
| Toluate | 0.11 |
| o-Cresol | 1.48 |
| m-Cresol | 1.6 |
| p-Cresol | 1.46 |
| 2-Chlorophenol | 0.42 |

Expression of phenol hydroxylase in the recombinant bearing pPH229 is induced by phenol and even more strongly by cresols. Since the BR219 phenol hydroxylase is also active on cresols, degradation of cresols in the environment may be an important function of the pathway. The lack of phenol hydroxylase induction in transformants pPH219-5, pPH222, pPH223, and pPH224, which contain the catechol 2,3-dioxygenase gene and/or DNA segments upstream of the pheA gene, is not yet understood but suggests a complex regulatory mechanism which may involve the small ORF designated R adjacent to pheA.

The recombinant *Escherichia coli* containing a gene encoding the phenol hydroxylase had the ability to produce indigo and indirubin. This result was unexpected since there was no evidence of this result in *Bacillus Stearothermophilus*. The results can be seen from the following examples.

EXAMPLE 2

This Example shows the production of indigo and indirubin.

*Escherichia coli* XL-1 constructs containing plasmids pPH219, pPH222, pPH223, or pPH224 were grown in LB broth (Example 1) containing 1 mM phenol and 50 micrograms per ml ampicillin for 24 hours as 50 ml cultures in a 125 ml flask with shaking at 37° C. The cultures containing bacterial cells and insoluble pigment were centrifuged at 10,000 rpm in a Sorvall SS34 Rotor (Dupont/Sorvall, Wilmington, Del.) for 10 minutes, and following removal of supernatant, the precipitate was extracted with 10 ml chloroform and centrifuged again. When measured using visible absorption spectroscopy, the purple supernatant showed absorption bands at both 560 and 610 nm. Upon paper chromatography, blue and pink bands were resolved which were identified as indigo and indirubin, respectively following extraction from the chromatogram and examination with combined gas chromatography and mass spectrometry.

EXAMPLE 3

This Example show kinetics of indigo and indirubin formation

The amount of indigo and indirubin produced in culture is dependent on the culture age, with indigo produced preferentially at earlier times when more dissolved oxygen is available. *E. coli* XL-1 containing pPH219 was grown in 50 ml LB culture containing 50 mg/ml ampicillin and 1 mMphenol. Production of indigo and indirubin was observed by visible spectral analysis following solubilization of the formed pigments in chloroform as described in Example 2.

TABLE 3

Production of indigo and indirubin with time in culture

| Culture Time (h) | OD (610) | OD (560) | Ratio |
|---|---|---|---|
| 18 | 0.025 | 0.016 | 1.56 |
| 24 | 0.695 | 0.590 | 1.78 |
| 30 | 0.660 | 0.706 | 0.934 |
| 42 | 0.536 | 0.727 | 0.74 |

As can be seen in Table 3, indigo with maximum absorption at 610 nm is produced in highest quantity at 24 h, whereas indirubin with maximum absorption at 560 nm is produced in highest quantity after 40 hours.

EXAMPLE 4

Influence of dissolved oxygen on formation of indigo and indirubin

The indigo/indirubin ratio produced varied with the oxygen available to the culture and could be regulated in this manner. This was observed by coloration of colonies of the constructs in Example 2 growth on LB agar plates which also contained 1 mM phenol and 50 µg/ml ampicillin. The center of the colonies were pink, whereas the outer edges were blue where oxygen was present. This effect could also be observed in liquid culture by altering culture oxygenation by using different volumes of culture medium for growth in identical flasks. For this purpose, *E. coli* XL-1 containing plasmid pPH219 was grown in 125 ml flasks containing varied amounts of LB medium supplemented with ampicillin at 50 µg/ml and phenol at 1 mM were grown at 37° C. for 24 hours followed by extraction of the pigments into chloroform as described in Example 2. As shown in Table 4 for pPH219, the ratio of absorption at 610 nm (the absorption maximum for indigo) to that at 560 nm (the absorption maximum for indirubin) varied with the culture volume, with the most highly aerated cultures with small volume producing the highest amounts of indigo.

TABLE 4

Variation in indigo and indirubin formation with culture aeration.

| Culture Volume (ml) | RATIO OD (610 nm)/ OD (560 nm) |
|---|---|
| 10 | 0.88 |
| 20 | 0.88 |
| 30 | 0.66 |
| 40 | 0.33 |
| 50 | 0.29 |
| 60 | 0.28 |
| 70 | 0.27 |
| 80 | 0.30 |
| 100 | 0.28 |

The phenol hydroxylase of the present invention derived from *Bacillus stearothermophilus* is monooxygenase and is stable at elevated temperatures. The prior art naphthlene dioxgenase from *Pseudomonas putida* tends to be unstable as reported in the literature and is composed of multiple units.

It is believed that tryptophan is converted to indole by tryptophanase in the *E. coli* by an oxidation mechanism. The coupling takes place without any other added precursors. Thus the *E. coli* must be able to produce tryptophan either naturally or by transformation.

As seen from Table 1, the presence of the phenol hydroxylase gene allows the production of indigo and indirubin even without the phenolic compound. The use of the phenolic compound is preferred.

The foregoing description is only illustrative of the present invention and the present invention is limited only by the hereinafter appended claims.

---

We claim:

1. A process for preparation of indigo and indirubin dyes which comprises:
   growing a recombinant *Escherichia coli* containing a gene from *Bacillus stearothermophilus* encoding phenol hydroxylase in an aqueous growth medium so that indigo and indirubin are produced.

2. The process of claim 1 wherein the gene is contained in a plasmid in an *E. coli* deposited as ATCC 69891.

3. The process of claim 1 wherein the *Bacillus stearothermophilus* is deposited as ATCC 67824.

4. The process of claim 1 wherein the phenol hydroxylase gene encoding the phenol hydroxylase has a DNA sequence essentially as set forth in SEQ ID NO:1.

5. The process of claim 1 wherein the medium contains a phenolic compound selected from the group consisting of phenol, cresol and 2-chlorophenol.

6. The process of claim 1 wherein the phenol hydroxylase has an amino acid sequence essentially as set forth in SEQ ID NO:1.

7. The process of claim 5 wherein the phenolic compound is a cresol.

8. The process of claim 1 wherein the indigo and indirubin are isolated from the aqueous solution with a solvent.

9. The method of claim 8 wherein the solvent is chloroform.

* * * * *

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
        ( A ) LENGTH: 1573
        ( B ) TYPE: Nucleic Acid
        ( C ) STRANDEDNESS: Single
        ( D ) TOPOLOGY: Linear     ( i i ) MOLECULE TYPE: DNA     ( i i i ) HYPOTHETICAL: No     ( i v ) ANTI-SENSE: No     ( v ) FRAGMENT TYPE:

( v i ) ORIGINAL SOURCE:
        ( A ) ORGANISM: Bacillus stearothermophilus
        ( B ) STRAIN: ATCC 67824
        ( C ) INDIVIDUAL ISOLATE: N/A
        ( D ) DEVELOPMENTAL STAGE: N/A
        ( E ) HAPLOTYPE: N/A
        ( F ) TISSUE TYPE: N/A
        ( G ) CELL TYPE: N/A
        ( H ) CELL LINE: N/A ( I ) ORGANELLE: N/A ( v i i ) IMMEDIATE SOURCE: N/A ( v i i i ) POSITION IN GENOME: N/A ( i x ) FEATURE:
    ( A ) NAME/KEY: encodes phenol hydroxylase
         pheA
    ( B ) LOCATION:
    ( C ) IDENTIFICATION METHOD: sequencing
    ( D ) OTHER INFORMATION:

( x ) PUBLICATION INFORMATION:
    ( A ) AUTHORS: Kim, Cheol, Oriel, Patrick J.
    ( B ) TITLE: Characterization of the
        Bacillus stearothermophilus
        BR219 Phenol Hydroxylase Gene
    ( C ) JOURNAL: American Society for Microbiology
    ( D ) VOLUME: 61
    ( E ) ISSUE: 4
    ( F ) PAGES: 1252-1256
    ( G ) DATE: 1995
    ( K ) RELEVANT RESIDUES IN SEQ ID NO: In SEQ ID NO: 1 From 1 to
        1260.

( x i ) SEQUENCE DESCRIPTION: SEQ ID NO:1:

```
ATG GAA AAA AAT AAA ATG TTA ATA GAA GAA AAG TTG GAC ACT GCT          45
Met Glu Lys Asn Lys Met Leu Ile Glu Glu Lys Leu Asp Thr Ala
                 5                  10                  15

GCT CTT CTT GCT AAG GCG GAG GAA ATA GGC CGG ATT GCT GAG GAA          90
Ala Leu Leu Ala Lys Ala Glu Glu Ile Gly Arg Ile Ala Glu Glu
                20                  25                  30

GAG GCG GGT GAA GCG GAC CGC AAT GCC TGT TTC TCC GAC CGG GTG         135
Glu Ala Gly Glu Ala Asp Arg Asn Ala Cys Phe Ser Asp Arg Val
                    35                  40                  45

GCT AGG GCC ATT AAA GAA GCT GGA TTC CAC AAG CTC ATG CGT CCC         180
Ala Arg Ala Ile Lys Glu Ala Gly Phe His Lys Leu Met Arg Pro
                50                  55                  60

AAG CAG TAC GGA GGA CTG CAA GTA GAC TTG CGA ACT TAC GGG GAG         225
Lys Gln Tyr Gly Gly Leu Gln Val Asp Leu Arg Thr Tyr Gly Glu
                    65                  70                  75

ATT GTC CGC ACA GTG GCC CGG TAC AGT GTT GCC GCA GGA TGG CTG         270
Ile Val Arg Thr Val Ala Arg Tyr Ser Val Ala Ala Gly Trp Leu
                    80                  85                  90

ACC TAT TTT TAT TCC ATG CAT GAG GTT TGG GCT GCA TAT CTG CCT         315
Thr Tyr Phe Tyr Ser Met His Glu Val Trp Ala Ala Tyr Leu Pro
                    95                  100                 105

CCA AAA GGC AGA GAA GAA ATT TTT GGA CAA GGA GGG CTG TTG GCA         360
Pro Lys Gly Arg Glu Glu Ile Phe Gly Gln Gly Gly Leu Leu Ala
                   110                 115                 120

GAC GTC GTT GCC CCT GTT GGC CGG GTG GAG AAG GAC GGG GAC GGC         405
Asp Val Val Ala Pro Val Gly Arg Val Glu Lys Asp Gly Asp Gly
                   125                 130                 135

TAC CGT CTC TAT GGG CAG TGG AAC TTC TGT AGC GGT GTC CTC CAT         450
Tyr Arg Leu Tyr Gly Gln Trp Asn Phe Cys Ser Gly Val Leu His
                   140                 145                 150

AGT GAC TGG ATC GGA CTT GGC GCC ATG ATG GAG CTG CCT GAC GGC         495
Ser Asp Trp Ile Gly Leu Gly Ala Met Met Glu Leu Pro Asp Gly
                   155                 160                 165

AAT AGT CCT GAG TAC TGT TTG TTA GTG CTG CCT AAG TCG GAT GTC         540
Asn Ser Pro Glu Tyr Cys Leu Leu Val Leu Pro Lys Ser Asp Val
                   170                 175                 180

CAG ATC GTA GAA AAT TGG GAT ACC ATG GGC CTC CGC GCT TCG GGA         585
Gln Ile Val Glu Asn Trp Asp Thr Met Gly Leu Arg Ala Ser Gly
                   185                 190                 195
```

```
AGC AAC GGG GTA TTA GTT GAA GGT GCT TAT GTT CCA TTA CAC CGG        630
Ser Asn Gly Val Leu Val Glu Gly Ala Tyr Val Pro Leu His Arg
            200                 205                 210

ATC TTT CCG GCT GGC CGG GTG ATG GCT CAT GGG AAG CCA GTG GGA        675
Ile Phe Pro Ala Gly Arg Val Met Ala His Gly Lys Pro Val Gly
            215                 220                 225

GGC GAT TAC GAC GAG AAT GAT CCG GTA TAT CGC ATG CCA TTT ATG        720
Gly Asp Tyr Asp Glu Asn Asp Pro Val Tyr Arg Met Pro Phe Met
            230                 235                 240

CCG CTT TTC TTG CTT GGG TTC CCT TTA GTA TCT TTA GGC GGC GAC        765
Pro Leu Phe Leu Leu Gly Phe Pro Leu Val Ser Leu Gly Gly Asp
            245                 250                 255

GAA CGA TTG GTG TCA CTT TTC CAA GAA CGC ACT GAG AAG CGC ATT        810
Glu Arg Leu Val Ser Leu Phe Gln Glu Arg Thr Glu Lys Arg Ile
            260                 265                 270

CGT GTC TTC AAA GGC GGC GCG AAA GAA AAG GAT TCT GCC GCT AGC        855
Arg Val Phe Lys Gly Gly Ala Lys Glu Lys Asp Ser Ala Ala Ser
            275                 280                 285

CAG CGG CTG TTA GCC GAG ATG AAA ACA GAA TTA AAT GCA ATG GAA        900
Gln Arg Leu Leu Ala Glu Met Lys Thr Glu Leu Asn Ala Met Glu
            290                 295                 300

GGC ATT GTG GAA CAA TAT ATC CGC CAG CTT GAG GCT TGC CAA AAA        945
Gly Ile Val Glu Gln Tyr Ile Arg Gln Leu Glu Ala Cys Gln Lys
            305                 310                 315

GAA GGA AAG ACG GTG ATG AAC GAT ATG GAG CGA GAG CAG CTA TTC        990
Glu Gly Lys Thr Val Met Asn Asp Met Glu Arg Glu Gln Leu Phe
            320                 325                 330

GCA TGG CGT GGA TAT GTG GCA AAA GCG TCC GCC AAT ATT GCC GTC        1035
Ala Trp Arg Gly Tyr Val Ala Lys Ala Ser Ala Asn Ile Ala Val
            335                 340                 345

AGA ACA CTG TTA ACT CTT GGA GGC AAT TCG ATC TTT AAA GGC GAT        1080
Arg Thr Leu Leu Thr Leu Gly Gly Asn Ser Ile Phe Lys Gly Asp
            350                 355                 360

CCG GTA GAA CTG TTC ACA AGA GAT TTG CTA GCG GTG GCC GCA CAT        1125
Pro Val Glu Leu Phe Thr Arg Asp Leu Leu Ala Val Ala Ala His
            365                 370                 375

CCT AAC TCC CTG TGG GAG GAT GCG ATG GCT GCA TAT GGA AGA ACG        1170
Pro Asn Ser Leu Trp Glu Asp Ala Met Ala Ala Tyr Gly Arg Thr
            380                 385                 390

ATA TTC GGG CTG CCA GGG GAC CCA GTC TGG TAAGACAGCA GCAGAATGTG      1220
Ile Phe Gly Leu Pro Gly Asp Pro Val Trp
            395                 400

TGTTTATAAA GATTTCAAA  AAATTCATTT  CTTTGGTGAA  AGAAAATGGA  TTTCACACAA  1280

AATTTAAACC AATGAACCCA ATTGGATCGT  TCGCGTCCAT  TTCACCAATA  TACAAAAAAA  1340

CAGCAGAAAA GGAGACGGAT ACCGGTGGAT  GACCGTTTGT  TTCGCAACGT  AATGGGGACA  1400

TTTGCCACAG GGGTGACAGT CATAACGACA  GAGATCGACG  GGGATATACA  CGGCATGACT  1460

GCAAATGCGT TTATGTCCGT ATCGTTACAT  CCAAAATTGG  TGCTTATTTC  GATTGGCGAA  1520

AAAGCAAAGA TGCGGGAGCG TATCAAAAAA  TCGAAAACGT  ATGCAGTAAG  CTT         1573
```